United States Patent [19]
Kilgrow et al.

[11] Patent Number: 5,472,081
[45] Date of Patent: Dec. 5, 1995

[54] NEEDLE HOLDER FOR A SUTURE PACKAGE

[75] Inventors: Bret J. Kilgrow; Stanley L. Mish, both of Flagstaff, Ariz.

[73] Assignee: W. L. Gore & Associates, Inc., Newark, Del.

[21] Appl. No.: 243,439

[22] Filed: May 16, 1994

Related U.S. Application Data

[60] Continuation of Ser. No. 975,493, Jan. 19, 1993, abandoned, which is a division of Ser. No. 801,552, Dec. 2, 1991, Pat. No. 5,192,483.

[51] Int. Cl.⁶ .................................................... A61B 17/06
[52] U.S. Cl. .................... 206/63.3; 206/382; 206/383
[58] Field of Search ................................. 206/63.3, 382, 206/383, 477, 478, 480, 483

[56] References Cited

U.S. PATENT DOCUMENTS

| | | | |
|---|---|---|---|
| 3,822,783 | 7/1974 | Mortensen | 206/480 |
| 3,972,418 | 8/1976 | Schuler et al. | 206/382 |
| 4,411,361 | 10/1983 | Mentzer | 206/480 |
| 4,424,898 | 1/1984 | Thyen et al. | 206/63.3 |
| 4,669,271 | 10/1987 | Lincoln et al. | |
| 4,699,271 | 10/1987 | Lincoln et al. | 206/63.3 |
| 4,860,895 | 8/1989 | Iaslovits | 206/480 |
| 4,961,498 | 10/1990 | Kalinski et al. | 206/480 |
| 5,056,658 | 10/1991 | Sobel et al. | |
| 5,131,533 | 7/1992 | Alpern | 206/63.3 |
| 5,192,483 | 3/1993 | Kilgrow et al. | 206/63.3 |

FOREIGN PATENT DOCUMENTS

| | | | |
|---|---|---|---|
| 113882 | 12/1899 | Germany. | |
| 2618662 | 11/1977 | Germany. | |
| 3016606 | 11/1981 | Germany | 206/382 |
| 9117713 | 11/1991 | WIPO. | |

*Primary Examiner*—David T. Fidei
*Attorney, Agent, or Firm*—Wayne D. House

[57] ABSTRACT

A suture needle holder for a suture package intended to contain an armed suture, comprising a sheet of planar plastic having at least one raised pedestal formed therein, said at least one raised pedestal having at least one slot therein oriented orthogonal to the sheet of planar plastic, said at least one slot having an open portion and a needle-holding portion releasably holding a portion of the length of a suture needle therein with the length of the suture needle lying in a plane parallel to the sheet of planar plastic, wherein the open portion of the slot is of a width narrower than the diameter of the length portion of the suture needle held within the needle-holding portion of the slot. A method of forming the suture needle holder is also described.

12 Claims, 10 Drawing Sheets

NEEDLE HOLDER FOR A SUTURE PACKAGE

CROSS-REFERENCE TO RELATED APPLICATIONS

This application is a continuation of application Ser. No. 07/975,493, filed Jan. 19, 1993, abandoned, which is a divisional of application Ser. No. 07/801,552, filed Dec. 2, 1991, now U.S. Pat. No. 5,192,483, issued Mar. 9, 1993.

FIELD OF THE INVENTION

This invention relates to the field of suture needle holders useful for packaging armed sutures.

BACKGROUND OF THE INVENTION

Suture packages containing armed sutures typically incorporate a means for securing the needle to the package so that the needle does not move while being grasped with suture forceps. The needle holder must also secure the needle from movement during shipping of the package, a requirement that prevents the needle point from possibly causing damage to the suture as well as preventing damage to the needle itself.

Needle holders for suture packages have taken many forms. Frequently, the point of the needle is inserted through a piece of plastic foam to hold it secure. The use of flaps cut from the packaging material is also common, the flap compressively holding the needle against the surface of the adjacent packaging material. Some flaps incorporate a slit through which a needle is placed, as taught by U.S. Pat. No. 4,884,681. Another alternative is described by U.S. Pat. No. 4,961,498, which involves a flexible rail and an adjacent post wherein a needle is held captive between the rail and post.

U.S. Pat. No. 4,424,898 teaches the construction of a needle holder incorporating adjacent pedestals having straight slots between the adjacent pedestals, wherein curved needles are fitted into the straight slots. The resulting interference due to the curvature of the needle retains the needle within the straight slot.

U.S. Pat. No. 4,699,271 describes a needle holder using two parallel ridges having pairs of shaped slots extending in predetermined curves across a U-shaped notch, wherein the curves are chosen to match the curvature of the needle intended to be fitted into a pair of slots.

SUMMARY OF THE INVENTION

The present invention relates to a suture needle holder for a suture package intended to contain an armed suture, comprising a sheet of planar plastic having at least one raised pedestal formed therein, the at least one raised pedestal having at least one slot therein oriented orthogonal to the sheet of planar plastic, the at least one slot having an open portion and a needle-holding portion releasably holding a portion of the length of a suture needle therein with the length of the suture needle lying in a plane parallel to the sheet of planar plastic, wherein the open portion of the slot is of a width narrower than the diameter of the length portion of the suture needle held within the needle-holding portion of the slot.

The needle holder is made by forming a sheet of planar plastic with a die having a flat surface, the die having at least one cavity cut into the flat surface for forming at least one pedestal into the sheet of planar plastic, the die further having at least one trough cut into the flat surface for holding a suture needle during forming of the sheet of planar plastic, the at least one trough intersecting the at least one cavity, the at least one trough having a depth less than the depth of the at least one cavity, wherein thermoforming techniques are used to apply heat and a pressure differential to the sheet of planar plastic to cause the sheet of planar plastic to form a pedestal into the cavity and to form a slot into the pedestal around the length portion of the suture needle lying in the intersection of the trough and the cavity. The pressure differential is preferably accomplished by vacuum forming wherein a vacuum is applied within the cavity or cavities of the die to form at least one slotted needle-holding pedestal into the planar plastic. The portion of the planar plastic intended to be formed into the pedestal should be heated to aid in the forming process. An additional portion of the planar plastic sheet material may be formed to package and retain the suture, such as by forming serpentine passageways into the planar plastic sheet. It is anticipated that the inventive needle-holder will be made as a part of a complete suture package capable of withstanding ordinary sterilization methods. Such a package would typically be enclosed in a protective bacteria impermeable envelope. The envelope may be partially or entirely made from a gas or steam permeable material for gas or steam sterilization. Because the sheet of planar plastic can function as an effective bacterial barrier in its own right, a practical package can be made by simply sealing a sheet of a protective bacteria impermeable material to the perimeter of the sheet of planar plastic. At least a portion of this sheet may also be made from a steam or gas permeable material if steam or gas sterilization is desired. Tyvek®, available from du Pont de Nemours, Inc. (Wilmington, Del.), is one such steam and gas permeable, bacteria impermeable sheet material.

The inventive needle holder capable of holding a range of needle sizes may be formed from a single die; further, the needle holder forming step is simultaneous with the packaging of the needle because the pedestal and slot are formed around the needle.

DETAILED DESCRIPTION OF THE INVENTION

Figure 1:
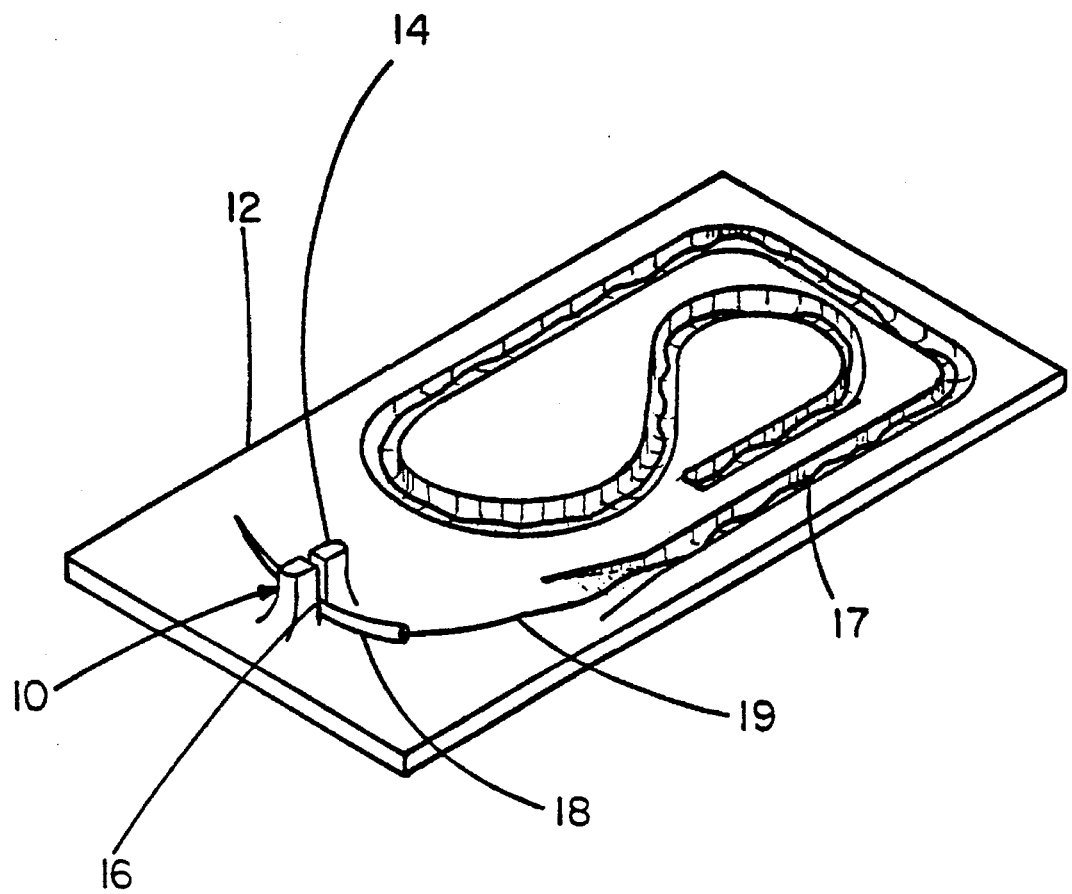
FIG. 1 describes a perspective view of a suture package made of a sheet of planar plastic and incorporating a suture needle holder of the present invention.

FIG. 1 describes a perspective view of a suture package made of a sheet of planar plastic and incorporating a suture needle holder of the present invention. It is apparent that the needle holder may be an integral part of a complete suture package.

The needle holder 10 is formed from a portion of a sheet 12 of planar plastic from which the entire package may be formed. The needle holder 10 comprises a raised pedestal 14 having at least one slot 16 formed therein to releasably retain a suture needle 18. The pedestal 14 and slot 16 are formed around the needle 18 during the packaging process so that a single forming die may be used to form needle holders for a wide variety of needle sizes.

An additional portion of the sheet of planar plastic 12 may be used to package and retain a length of suture 19 attached to the needle 18, such as by the use of a formed serpentine passageway 17.

Figure 1A:
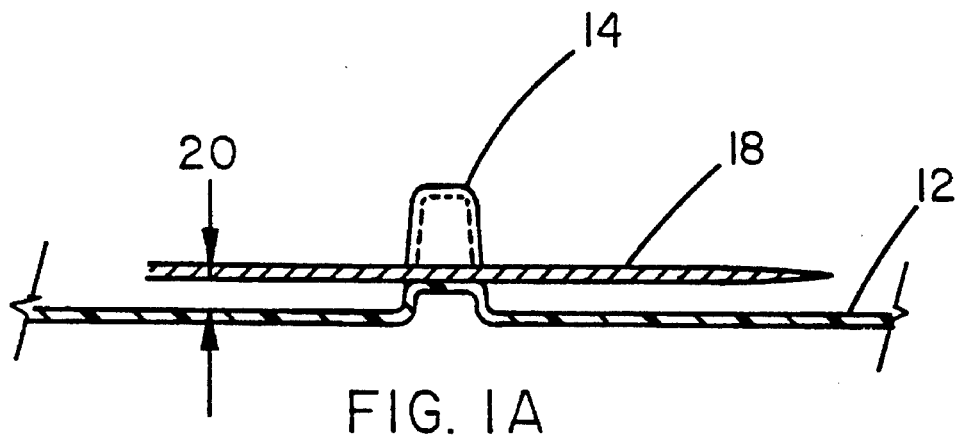
FIGS. 1A and 1B describe end and transverse cross sectional views respectively of the suture needle holder of the present invention.
Figure 1B:
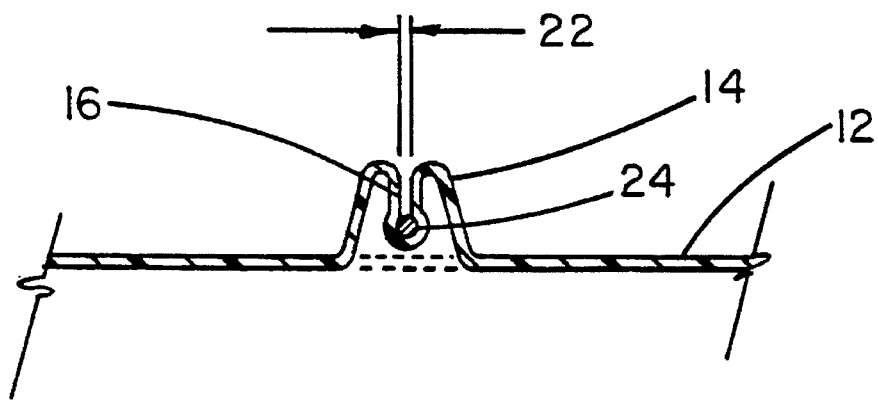

FIGS. 1A and 1B describe end and transverse cross sectional views respectively of the inventive needle holder. FIG. 1A shows that the pedestal 14 and slot 16 can be formed to hold the needle 18 in a way that provides a clearance 20 between the needle and the surface of the sheet 12 of planar plastic. The provision of clearance 20 allows improved ease of grasping of the needle 18 by conventional suture forceps. FIG. 1B shows that the width 22 of the slot 16 is made to be significantly narrower than the diameter of the needle portion 24 retained within the slot 16. The width 22 of the slot 16 should be about 5 to 95 percent of the diameter of the needle portion 24 intended to be retained by the slot 16. A more preferred range is for the slot width to be about 50 to 95 percent of the diameter of the retained needle portion. This relationship provides for adequately secure retention of the needle while allowing the needle to be easily removed with a minimum of force. The relationship between slot width and needle diameter is the result of the amount of heat and the quantity of pressure differential applied to the sheet of planar plastic during the forming process. The depth of the cavity extending beyond the depth of the trough can also affect this relationship.

It is believed that a useful needle holder of the present invention may be made using a thin sheet 12 of planar plastic wherein the two opposing sides of the slot 16 retaining the needle are actually in contact with each other but not thermally fused together, that is, the slot width is effectively 0 percent of the diameter of the retained needle portion 24.

The needle is typically removed from the needle holder by grasping an exposed portion of the needle with suture forceps and lifting it upwardly out of the slot in a direction generally orthogonal to the planar surface of the needle holder and suture package.

Figure 1C:
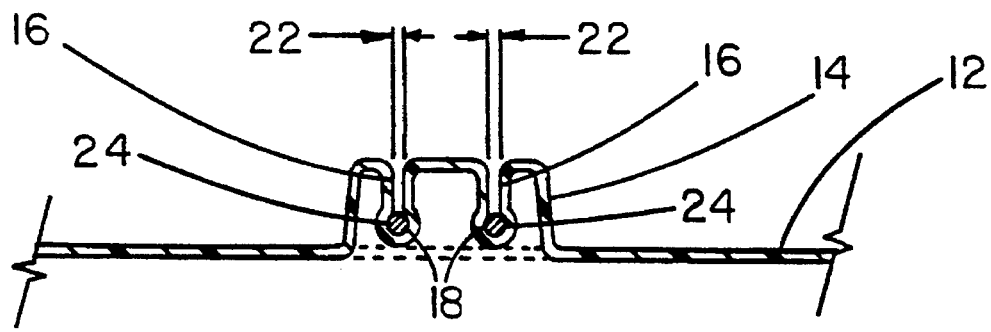
FIG. 1C describes a transverse cross sectional view of an alternative embodiment designed to hold two needles.

FIG. 1C describes a transverse cross sectional view of an alternative pedestal 14 providing two slots 16 for retaining two needles 18. It is apparent that as many needle retaining slots can be provided within a single pedestal 14 as desired as long as a practical amount of separation is provided between adjacent needles in order to allow for their individual removal.

Figure 2:
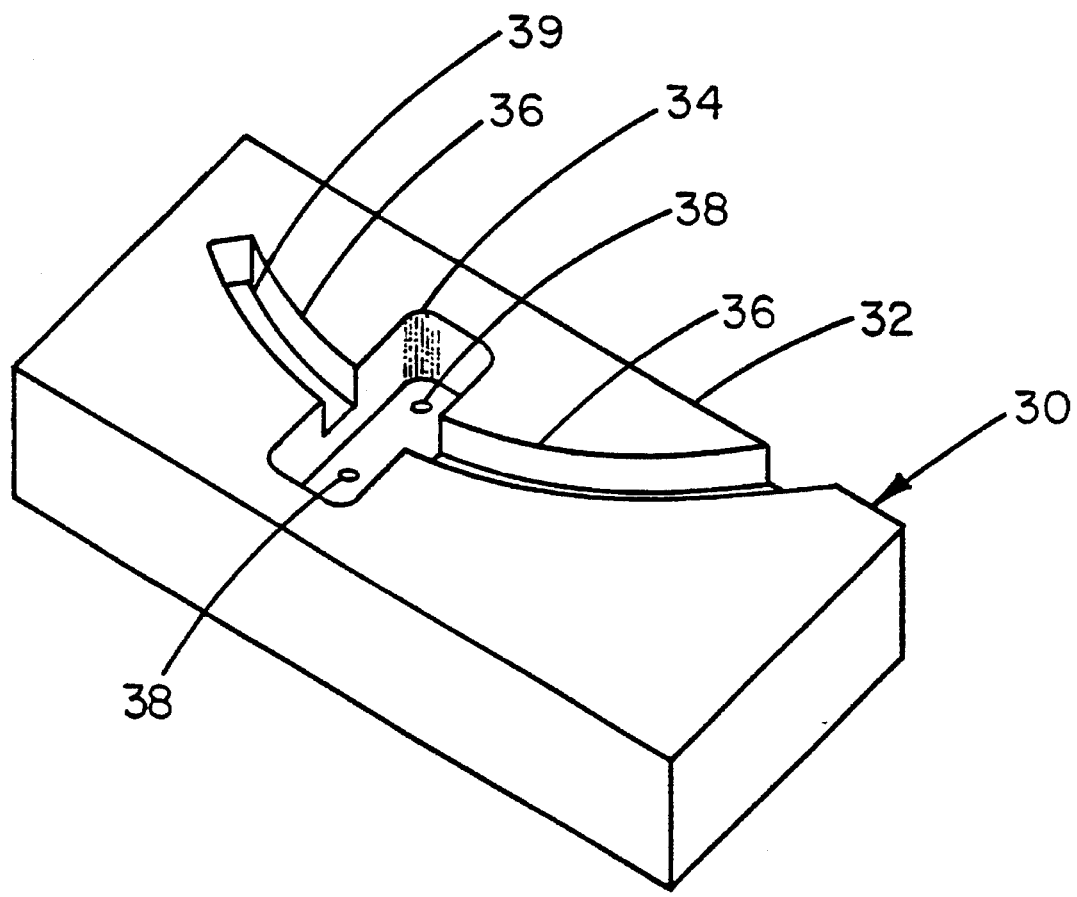
FIG. 2 describes a perspective view of a die useful for forming the suture needle holder of the present invention.

FIG. 2 describes a perspective view of a die for forming the needle holder of the present invention. The die 30 has a flat surface 32 on which the sheet of planar plastic intended to be formed is laid. The flat surface 32 is interrupted by a cavity 34 and a trough 36 which intersects the cavity 34. Cavity 34 is used to form the pedestal 14 of the needle holder 10 while the trough 36 holds the suture needle 18 during the forming process. As shown, the depth of cavity 34 must be greater than the depth of the trough 36. Cavity 34 preferably provides a means for producing a pressure differential across the two opposing surfaces of the sheet of planar plastic during the forming process such as vacuum ports 38. Alternatively, a positive pressure may be applied to the opposite side of the sheet of planar plastic during forming. Likewise, a positive pressure may be used simultaneously with a vacuum. Trough 36 should be of depth greater than the diameter of the needle portion 24 intended to be held by the slot 16 within the pedestal. The difference between the diameter of the needle portion 24 and the depth of the trough 36 will be the clearance 20 between the needle 18 and the surface of the sheet 12 of planar plastic in the finished needle holder 10. The floor 39 of the needle trough 36 may optionally be made of a magnetic material to aid in holding the needle 18 in place within the trough 36 during the forming process.

Figure 2A:
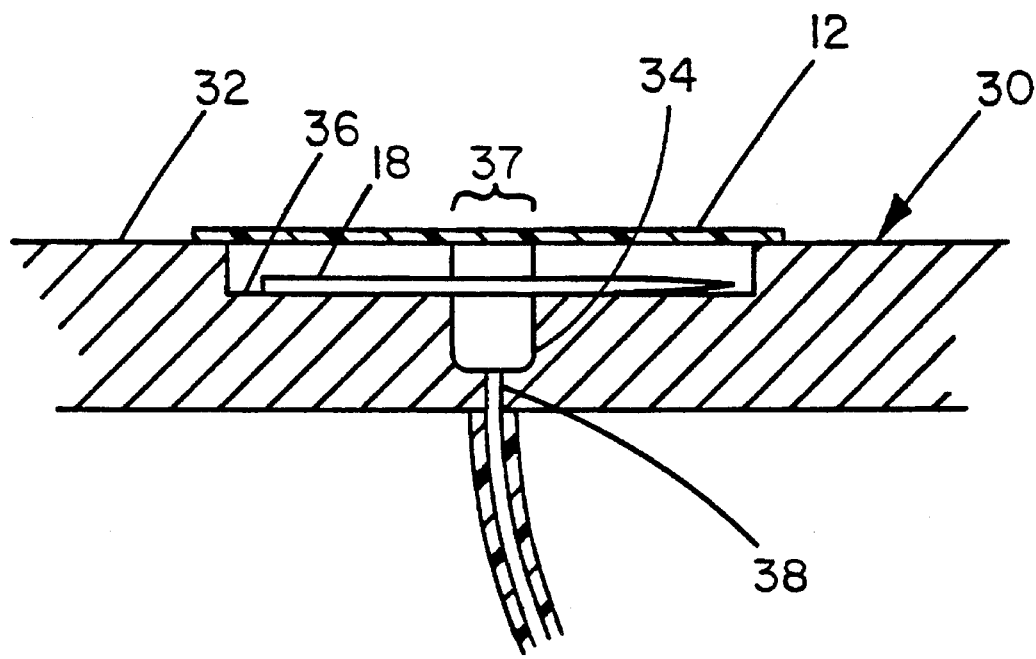
FIGS. 2A and 2B describe end and transverse cross sectional views respectively of the die of FIG. 2 containing a suture needle as intended for use during forming of the suture needle holder.
Figure 2B:
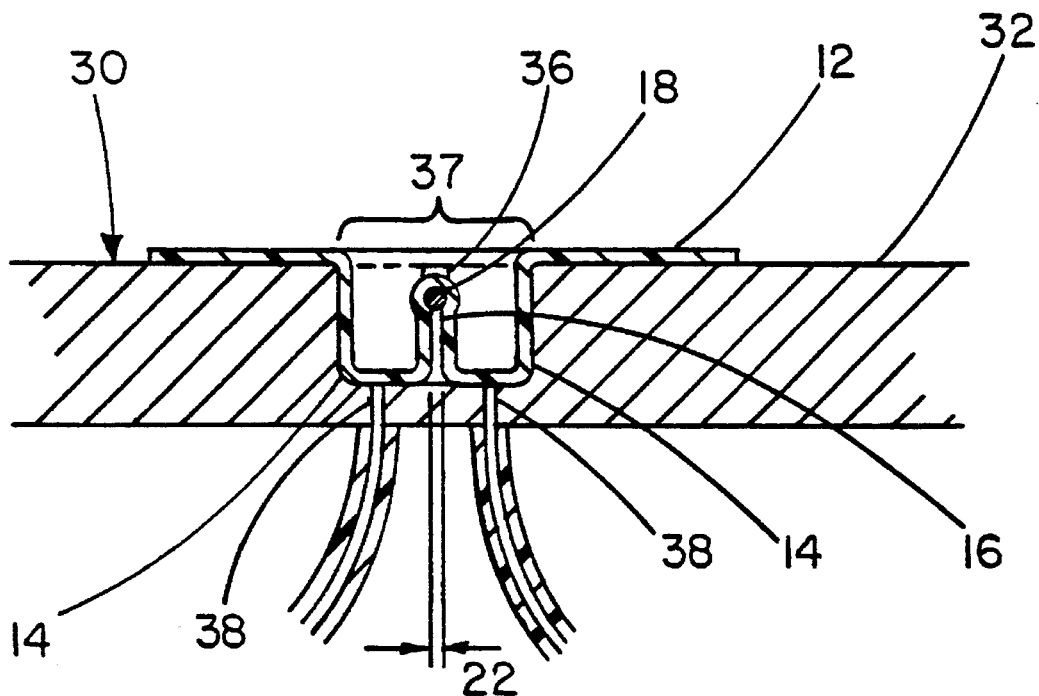

As shown by the end sectional view of FIG. 2A, the needle holder 10 is formed by placing a needle 18 into the trough 36 prior to placing a sheet 12 of planar plastic onto the flat surface 32 of the die 30. A pressure differential is created across the two opposing sides of the sheet 12 of planar plastic above the cavity 34 of the die 30, with the higher relative pressure applied to the portion 37 of the side of the sheet 12 of planar plastic opposing the cavity 34. This is preferably accomplished by pulling a vacuum within the cavity through optional vacuum ports 38 in the floor of the cavity. The portion 37 of the side of the sheet 12 of planar plastic intended to be deformed into the cavity 34 to form the pedestal 14 should be heated to aid in the forming process. The heat may be applied, for example, by hot air or by momentarily contacting the portion 37 of the side of the sheet 12 of planar plastic opposite the die cavity 34 with a heated metal shoe. The amount of heat and the time of its application are the most critical parameters in the needle holder forming process. As shown by the transverse cross sectional view of FIG. 2B, the presence of a suture needle 18 within the trough 36 and spanning the cavity 34 results in the formation of the pedestal 14 around the needle 18, simultaneously capturing the needle 18 and forming the slot 16 within the pedestal 14. The amount of pressure differential, heat and time of application, in conjunction with the thickness of the sheet 12 of planar plastic and the type of plastic used, will control the width 22 of the slot 16.

Figure 2C:
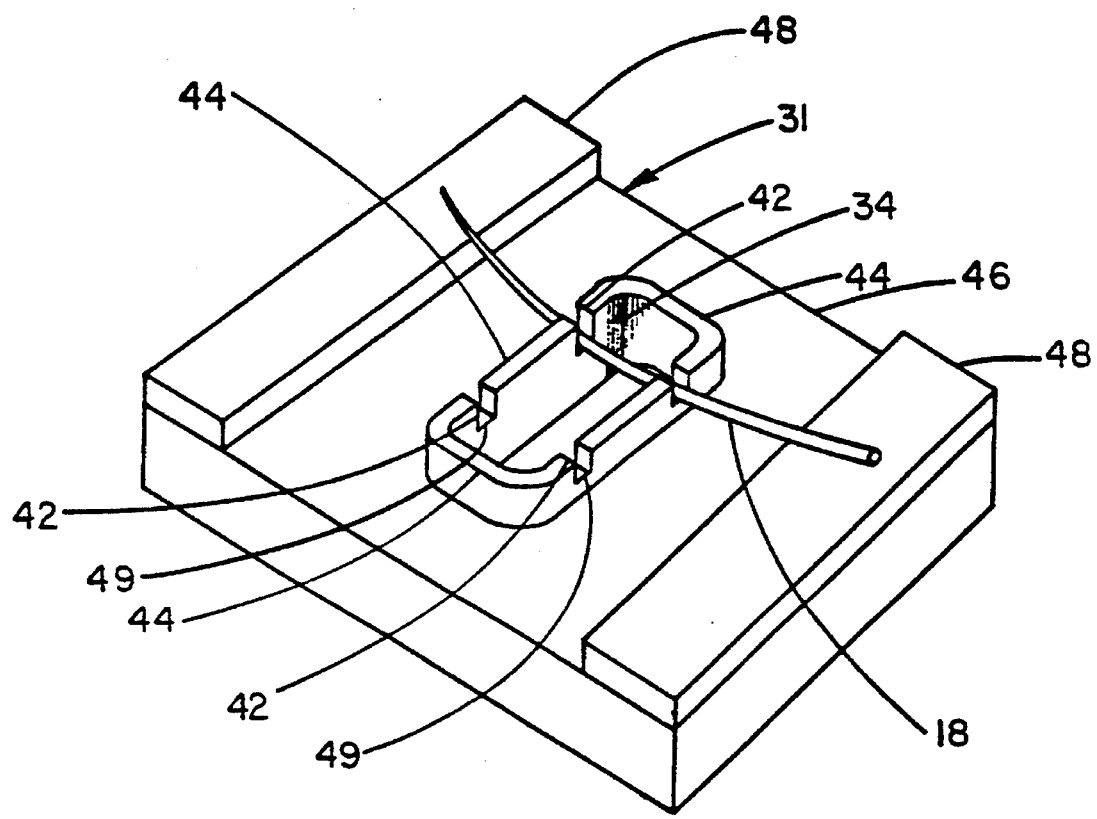
FIG. 2C describes a perspective view of an alternative die.

FIG. 2C describes an alternative die 31. In the embodiment shown, the die 31 incorporates two pairs of grooves 42 to allow it to produce a needle holder for retaining two needles. For clarity, only one needle 18 is shown held by one pair of grooves 42. It is apparent that a die may be configured with as many troughs 36 or pairs of grooves 42 as required to hold the desired number of needles 18. In the embodiment of FIG. 2C a rim 44 surrounds cavity 34. The depth of grooves 42 corresponds to the depth of trough 36 described previously. The flat surface 46 of the die surrounding rim 44 is recessed below the rim 44 only for convenience of placing the needle. The recession of the flat surface 46 is not intended to cause significant deformation of the planar plastic into this area and consequently there is no differential pressure or heat applied to the sheet of planar plastic immediately above flat surface 46 during the forming process. Magnets 48 are provided to hold the needles securely during the forming process; the surface of the magnets 48 should lie in the same plane as the floor 49 of the grooves 42.

The advantage of the die described by FIG. 2C is that it is able to accommodate a wider variety of needle shapes, from straight needles to highly curved needles. A die of the type shown by FIGS. 2, 2A and 2B incorporating a trough will only accommodate needles fitting the shape of the trough.

Figure 3A:
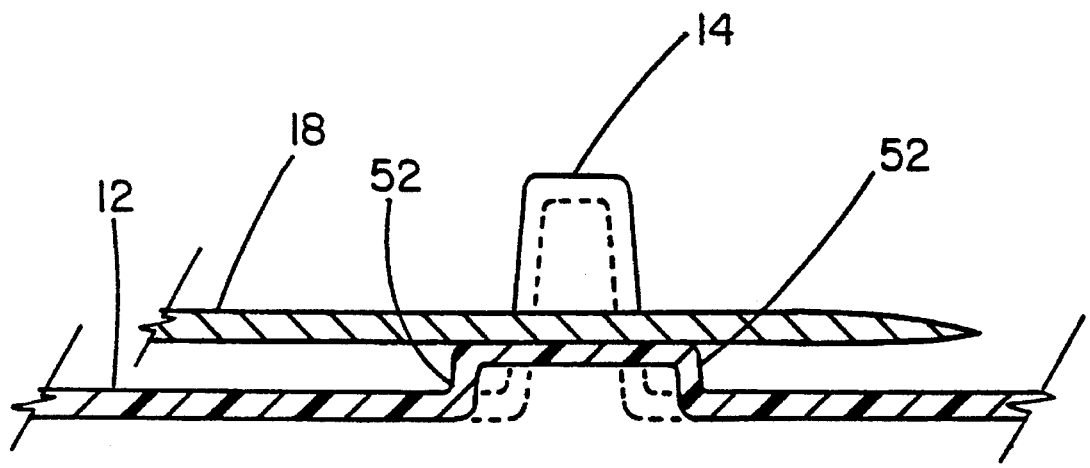
FIGS. 3A and 3B describe side and end and transverse cross sectional views respectively of an alternative embodiment of the suture needle holder incorporating supporting projections extending outwardly from the pedestal sides.
Figure 3B:
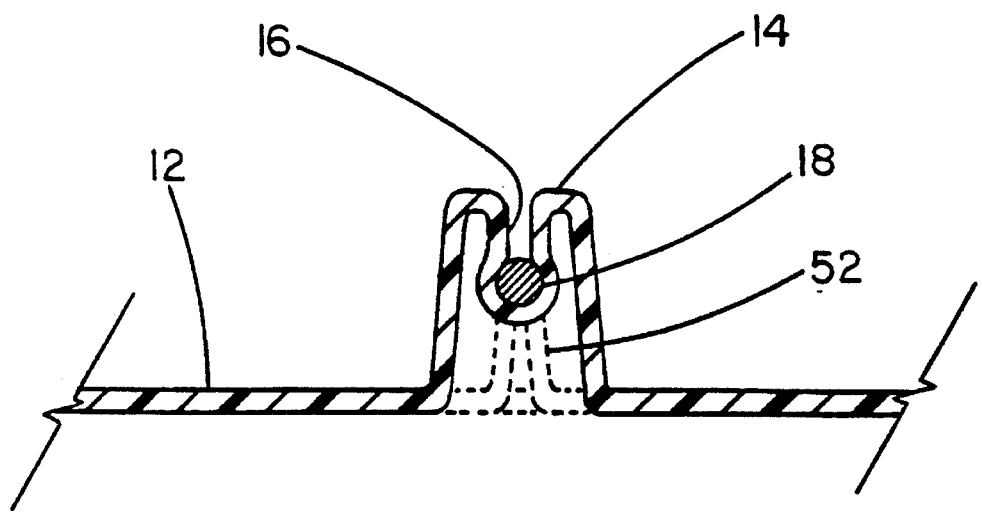

FIGS. 3A and 3B show end and transverse cross sectional views respectively of a variation of the needle holder wherein a supporting projection 52 extends outwardly away from the sides of the pedestal 14 and lies between a portion of the needle adjacent to the pedestal and the plane of the sheet 12 of planar plastic prior to forming. Supporting projection 52 results from deformation of the sheet 12 of planar plastic into the corresponding die space during forming. The supporting projection 52 is useful to further support the needle 18 and increase the stability of the needle within the needle holder.

Figure 4:
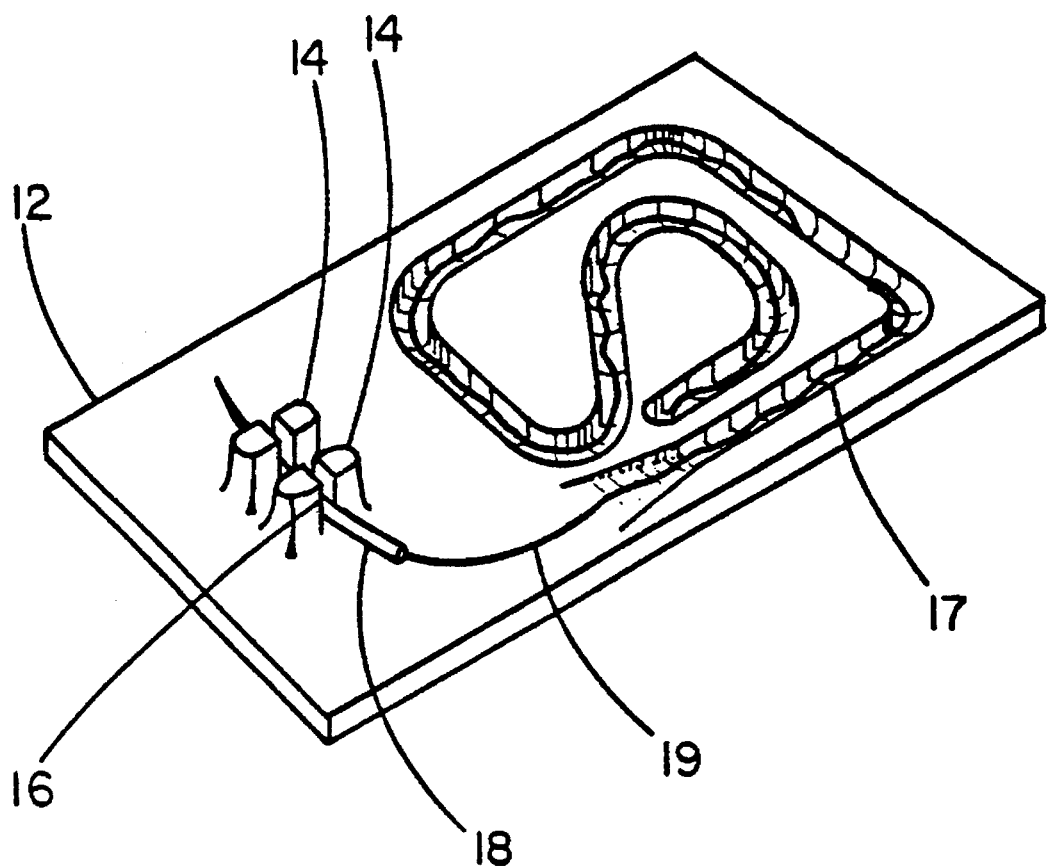
FIGS. 4 and 4A describe perspective and end sectional views of an alternative embodiment of the present invention incorporating a two-pedestal suture needle holder.
Figure 4A:
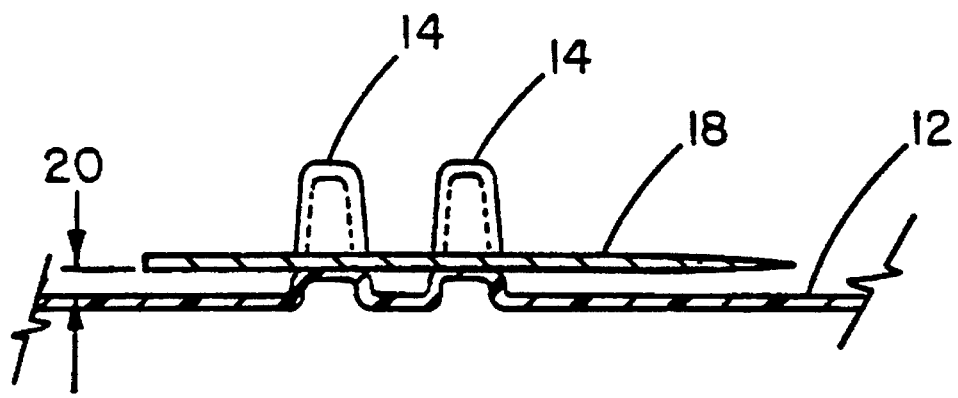

FIGS. 4 and 4A show perspective and end sectional views of an alternative embodiment of the needle holder wherein each needle 18 is held by two pedestals 14 with each pedestal having a slot for holding different length portions of the same needle 18. A needle holder incorporating two pedestals may be desirable when it is intended to make the center portion of the needle length available for grasping with suture forceps.

Figure 5A:
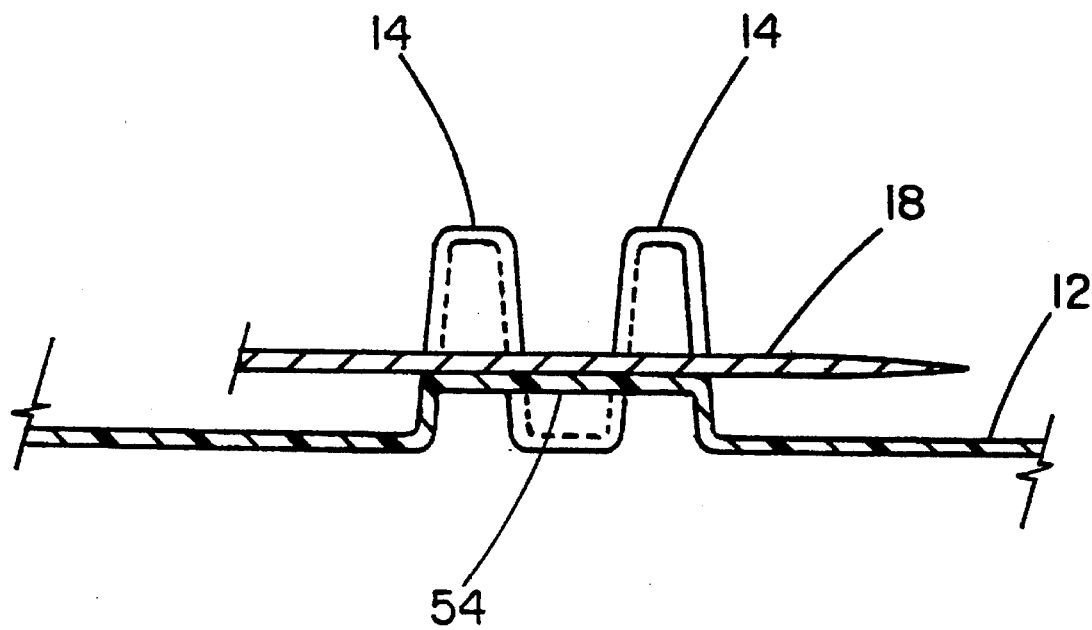
FIGS. 5A and 5B describe end and side transverse cross sectional views respectively of an alternative embodiment of the suture needle holder described in FIGS. 4 and 4A.
Figure 5B:
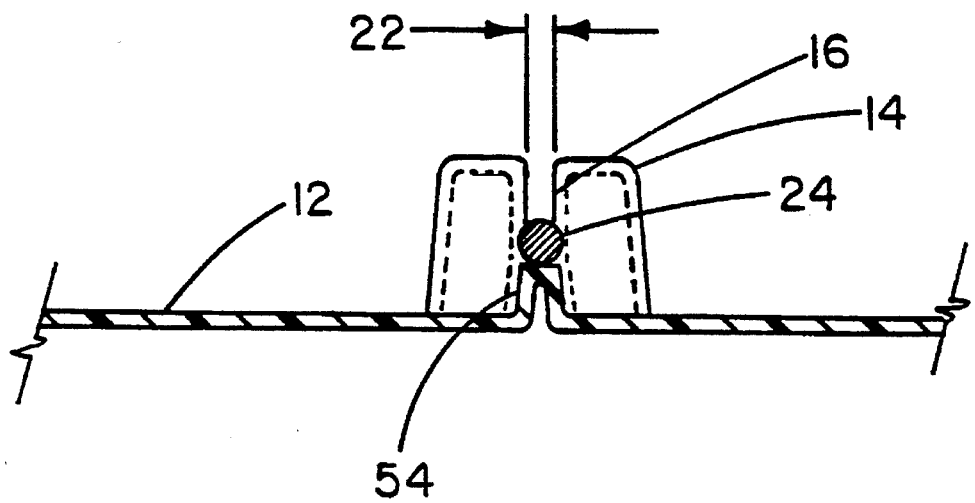

FIGS. 5A and 5B show end and transverse cross sectional views of a variation of the embodiment of FIGS. 4 and 4A wherein a supporting projection 54 extends between the pedestals into the space between the needle and the plane of the sheet of planar plastic prior to forming.

Figure 6:
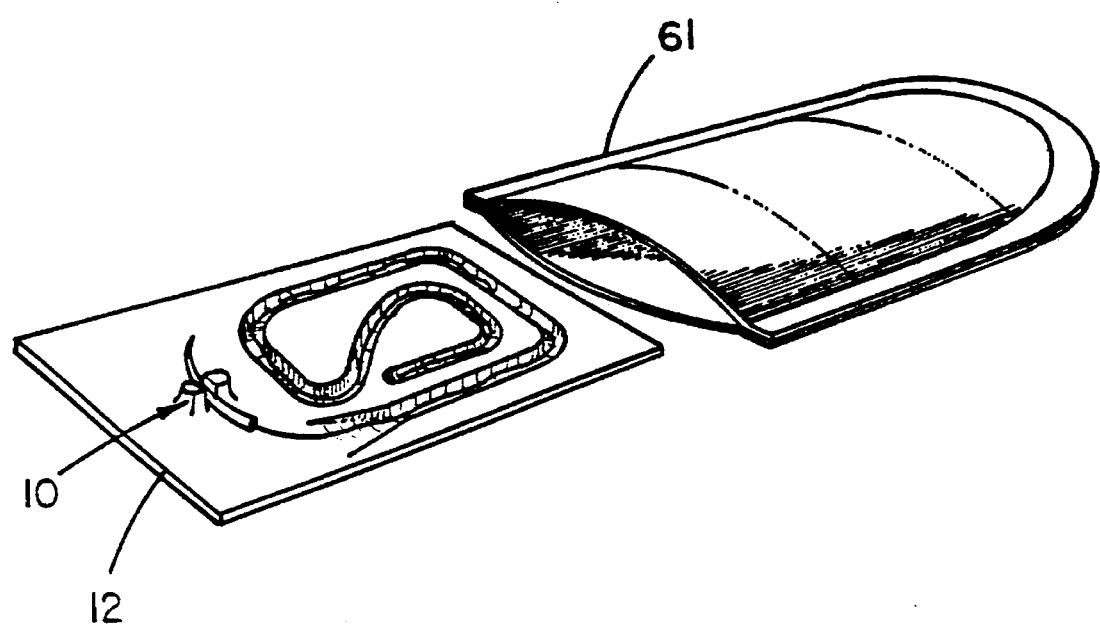
FIG. 6 describes a suture package incorporating the inventive needle holder, sealed within a protective bacteria impermeable envelope.
Figure 7:
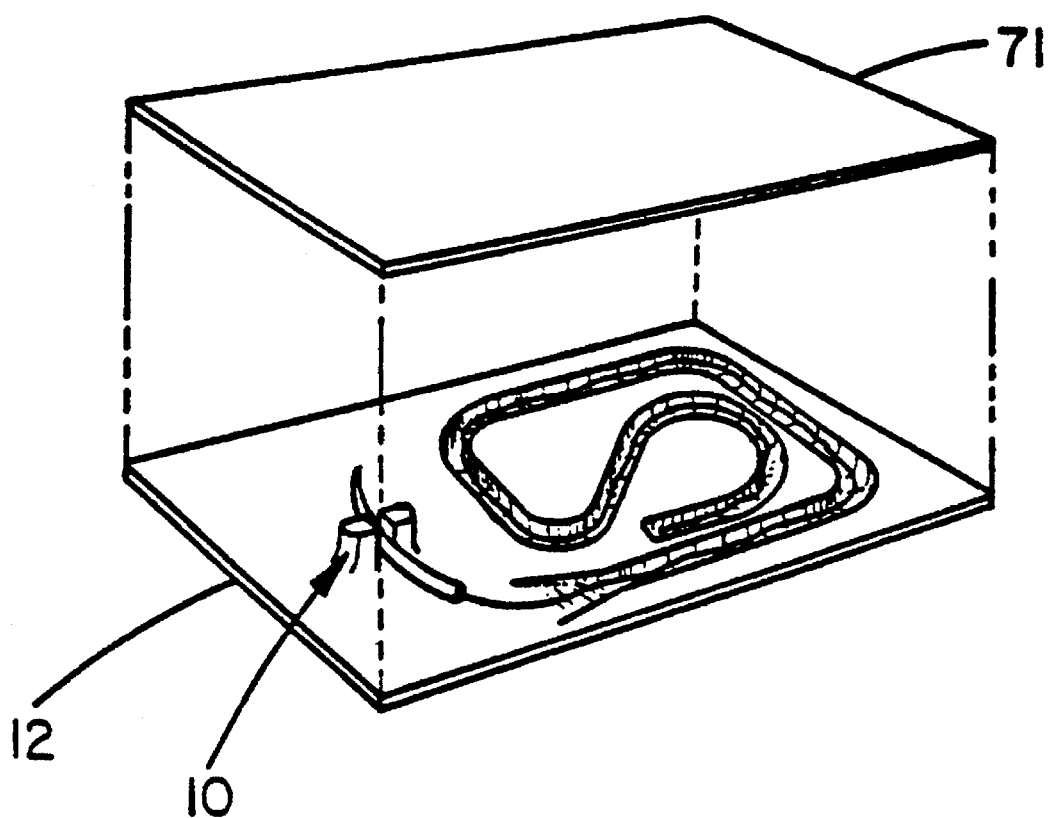
FIG. 7 describes a sterilizable suture package formed by sealing a sheet of protective bacteria impermeable material to the perimeter of the sheet of planar plastic from which the needle holder was formed.

FIG. 6 shows the needle holder as a part of an armed suture package enclosed by a protective envelope 61 intended to allow the suture and package to be sterilized and maintained sterile until the envelope is opened. The envelope 61 can be made at least partially from a steam and gas permeable, bacteria impermeable material if steam or gas sterilization is desired. FIG. 7 shows an alternative sterilizable suture package wherein a cover sheet 71 of protective bacteria impermeable material is sealed around the perimeter of the sheet 12 of planar plastic from which the needle holder was formed. The cover sheet 71 may be made at least partially from a steam and gas permeable material if steam or gas sterilization is desired. The sealed sterilizable packages represented by FIGS. 6 and 7 may additionally be sealed in outer protective envelopes (not shown) for mechanical and sterility protection until ready for use.

The suture needle holder and suture package may be formed from various types of thermoplastic sheet materials including polypropylene, polyethylene terephthalate, polycarbonate, polyethylene, polyvinyl chloride and polystyrene. It is also anticipated that formable metal foils may also be useful for the needle holder of the present invention using ordinary metal foil forming technology.

I claim:

1. A suture needle holder for a suture package comprising a sheet of planar plastic having at least one raised pedestal therein, said sheet of planar plastic having a substantially uniform thickness so that said at least one raised pedestal comprises the substantially uniform thickness, said at least one raised pedestal having at least one slot therein, said at least one slot comprising two opposing surfaces oriented orthogonal to the sheet of planar plastic, said at least one slot having an open portion and a needle-holding portion releasably holding a portion of the length of a suture needle therein with the length of the suture needle lying in a plane parallel to the sheet of planar plastic, wherein the portion of the length of the suture needle has a diameter and a surface, wherein the open portion of the slot is of a width narrower than the diameter of the portion of the length of the suture needle held within the needle-holding portion of the slot, wherein the two opposing surfaces of the at least one slot intersect the surface of the portion of the length of the suture needle, and wherein the two opposing surfaces are substantially symmetrical with each other in transverse cross section.

2. A suture needle holder according to claim 1 wherein the open portion of the slot is of width equal to about 5 to 95 percent of the diameter of the length portion of the suture needle held within the needle holding portion of the slot.

3. A suture needle holder according to claim 2 wherein the open portion of the slot is of width equal to about 50 to 95 percent of the diameter of the length portion of the suture needle held within the needle holding portion of the slot.

4. A suture needle holder according to claim 1 wherein said raised pedestal has two opposing sides oriented substantially orthogonal to the sheet of planar plastic and to the portion of the length of the suture needle, and wherein supporting projections extend outwardly away from the two opposing sides of the pedestal between the sheet of planar plastic and the portions of the suture needle adjacent to the pedestal.

5. A suture needle holder according to claim 1 having two raised pedestals.

6. A suture needle holder according to claim 5 wherein a supporting projection extends between the two raised pedestals and between the sheet of planar plastic and a portion of the suture needle between the two pedestals.

7. A suture needle holder according to claim 1 wherein the needle holder is a part of a suture package containing at least one suture which is attached to the suture needle.

8. A suture needle holder according to claim 1 wherein the sheet of planar plastic is selected from the group comprising polypropylene, polyethylene terephthalate, polycarbonate, polyethylene, polyvinyl chloride and polystyrene.

9. A suture needle holder according to claim 1 wherein the perimeter of the sheet of planar plastic has been sealed to a sheet of protective bacteria impermeable material.

10. A suture needle holder according to claim 9 wherein at least a portion of the sheet of protective bacteria impermeable material is made from a steam and gas permeable material.

11. A suture needle holder according to claim 1 wherein the needle holder has been sealed within a protective bacteria impermeable envelope to form a sealed package.

12. A suture needle holder according to claim 11 wherein the sealed package has been sterilized.

* * * * *